United States Patent
Mazmanian et al.

(10) Patent No.: US 11,896,629 B2
(45) Date of Patent: *Feb. 13, 2024

(54) PROBIOTIC THERAPIES FOR TREATING RETT SYNDROME

(71) Applicant: California Institute of Technology, Pasadena, CA (US)

(72) Inventors: Sarkis K Mazmanian, Porter Ranch, CA (US); Paul H Patterson, Altadena, CA (US); Janet Chow, Alhambra, CA (US); Elaine Hsiao, Rowland Heights, CA (US); Sara W McBride, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 518 days.

This patent is subject to a terminal disclaimer.

(21) Appl. No.: 16/935,837

(22) Filed: Jul. 22, 2020

(65) Prior Publication Data

US 2021/0000888 A1 Jan. 7, 2021

Related U.S. Application Data

(60) Continuation of application No. 15/249,870, filed on Aug. 29, 2016, now abandoned, which is a division of application No. 13/267,748, filed on Oct. 6, 2011, now Pat. No. 9,452,189.

(60) Provisional application No. 61/472,963, filed on Apr. 7, 2011, provisional application No. 61/391,004, filed on Oct. 7, 2010.

(51) Int. Cl.
*A61K 35/741* (2015.01)
*A61K 35/00* (2006.01)

(52) U.S. Cl.
CPC ........ *A61K 35/741* (2013.01); *A61K 2035/11* (2013.01)

(58) Field of Classification Search
CPC .. A61K 35/741; A61K 2035/11; A61K 35/74; A61K 2035/115; A61P 25/00; A61P 25/18; A61P 25/20; A61P 25/22; G01N 2800/28; G01N 33/6896

See application file for complete search history.

(56) References Cited

U.S. PATENT DOCUMENTS

| | | | |
|---|---|---|---|
| 5,443,826 A | 8/1995 | Brody | |
| 5,951,977 A | 9/1999 | Nisbet et al. | |
| 6,326,360 B1 | 12/2001 | Kanazawa et al. | |
| 7,041,814 B1 | 5/2006 | Weinstock et al. | |
| 7,731,976 B2 | 6/2010 | Cobb et al. | |
| 7,749,509 B2 | 7/2010 | Cobb et al. | |
| 8,192,733 B2 | 6/2012 | Cobb et al. | |
| 10,111,914 B2 | 10/2018 | Bailey et al. | |
| 10,124,025 B2 | 11/2018 | Hsiao et al. | |
| 10,200,089 B2 | 2/2019 | Hsiao et al. | |
| 2002/0013270 A1 | 1/2002 | Bolte | |
| 2004/0005304 A1 | 1/2004 | Brudnak | |
| 2004/0028689 A1 | 2/2004 | Borody | |
| 2004/0170617 A1 | 9/2004 | Finegold | |
| 2006/0167057 A1 | 7/2006 | Kong et al. | |
| 2006/0177424 A1 | 8/2006 | Cobb et al. | |
| 2007/0280911 A1 | 12/2007 | Cobb et al. | |
| 2009/0118257 A1 | 5/2009 | Jankowski et al. | |
| 2010/0303782 A1 | 12/2010 | Cobb et al. | |
| 2011/0081320 A1 | 4/2011 | Westall et al. | |
| 2011/0118135 A1 | 5/2011 | State et al. | |
| 2012/0190055 A1 | 7/2012 | Cezar et al. | |
| 2012/0207726 A1 | 8/2012 | Lipkin et al. | |
| 2012/0237482 A1 | 9/2012 | Rodriguez | |
| 2012/0252775 A1 | 10/2012 | Finegold | |
| 2013/0115257 A1 | 5/2013 | Gysemans et al. | |
| 2013/0195802 A1 | 8/2013 | Moore | |
| 2015/0050246 A1 | 2/2015 | Jones et al. | |
| 2016/0120916 A1 | 5/2016 | Hsaio et al. | |
| 2016/0193256 A1 | 7/2016 | Honda et al. | |
| 2016/0339065 A1 | 11/2016 | Adams et al. | |
| 2016/0375065 A1 | 12/2016 | Mazmanian et al. | |

*Primary Examiner* — Taeyoon Kim
*Assistant Examiner* — Tiffany M Gough
(74) *Attorney, Agent, or Firm* — Knobbe, Martens, Olson & Bear, LLP

(57) ABSTRACT

Provided is a method and a composition for improving behavioral performance in an individual comprising identifying an individual in need of treatment, and providing such an individual a composition comprising bacteria within the genus *Bacteroides*.

11 Claims, 5 Drawing Sheets

PROBIOTIC THERAPIES FOR TREATING RETT SYNDROME

CROSS-REFERENCE TO RELATED APPLICATIONS

This is a continuation application of U.S. patent application Ser. No. 15/249,870, filed on Aug. 29, 2016, which is a divisional application of U.S. patent application Ser. No. 13/267,748, filed on Oct. 6, 2011, which issued as U.S. Pat. No. 9,452,189 on Sep. 27, 2016, and which claims the benefit of Provisional Patent Application Nos. 61/391,004, filed on Oct. 7, 2010, and 61/472,963 filed on Apr. 7, 2011. The contents of these related applications are incorporated by reference herein in their entireties.

GOVERNMENT FUNDING/SUPPORT

This invention was made with government support under GM007616 awarded by the National Institutes of Health. The government has certain rights in the invention.

FIELD

The invention relates to probiotic and probiotic-based compositions and a method of using them. More particularly, it relates to the use of Bacteroides fragilis or related bacteria to improve the mental behavior of individuals suffering from autism, autism spectrum disorders (ASD) and/or conditions with related symptoms such as anxiety.

BACKGROUND

Autism spectrum disorders (ASDs) are complex neurodevelopmental disabilities characterized by repetitive/stereotypic behaviors and deficits in communication and social interaction. Recent studies highlight striking neural and peripheral immune dysregulation in autistic individuals. Moreover, a significant subset of ASD children exhibit gastrointestinal (GI) complications, including increased intestinal permeability and altered composition of intestinal microbiota. Furthermore, antibiotic treatment and restricted diets are reported to improve behavioral symptoms in some ASD children (reviewed by Buie et al., 2010).

BRIEF SUMMARY

In one embodiment, a method of improving behavioral performance in an individual is provided comprising, identifying an individual in need of treatment, and providing such an individual a composition comprising bacteria within the genus Bacteroides, whereby the individual shows improved behavioral performance.

In an embodiment, the individual in need of treatment suffers from anxiety, autism, ASD or a mental condition with some of the symptoms of ASD.

In another embodiment, the bacteria is selected from a group consisting of B. fragilis, B. theta, B. vulgatus, and B. faecalis.

In yet another embodiment, the bacteria is a mixture of several different species members within the genus Bacteroides.

In another embodiment, a probiotic composition for improving behavioral performance is provided comprising bacteria within the genus Bacteroides, whereby the individual shows improved behavioral performance.

In yet another embodiment, a nutraceutical for improving behavioral performance in individuals is provided comprising bacteria within the genus Bacteroides, whereby the individual shows improved behavioral performance.

In another embodiment, a pharmaceutical composition is provided comprising bacteria within the genus Bacteroides, and a pharmaceutically acceptable carrier, whereby the composition improves behavioral performance.

In another embodiment, the pharmaceutical composition further comprises another pharmaceutical or compound used to treat the behavioral performance, wherein the pharmaceutical or compound does not comprise any other bacteria.

DETAILED DESCRIPTION

Figure 1:
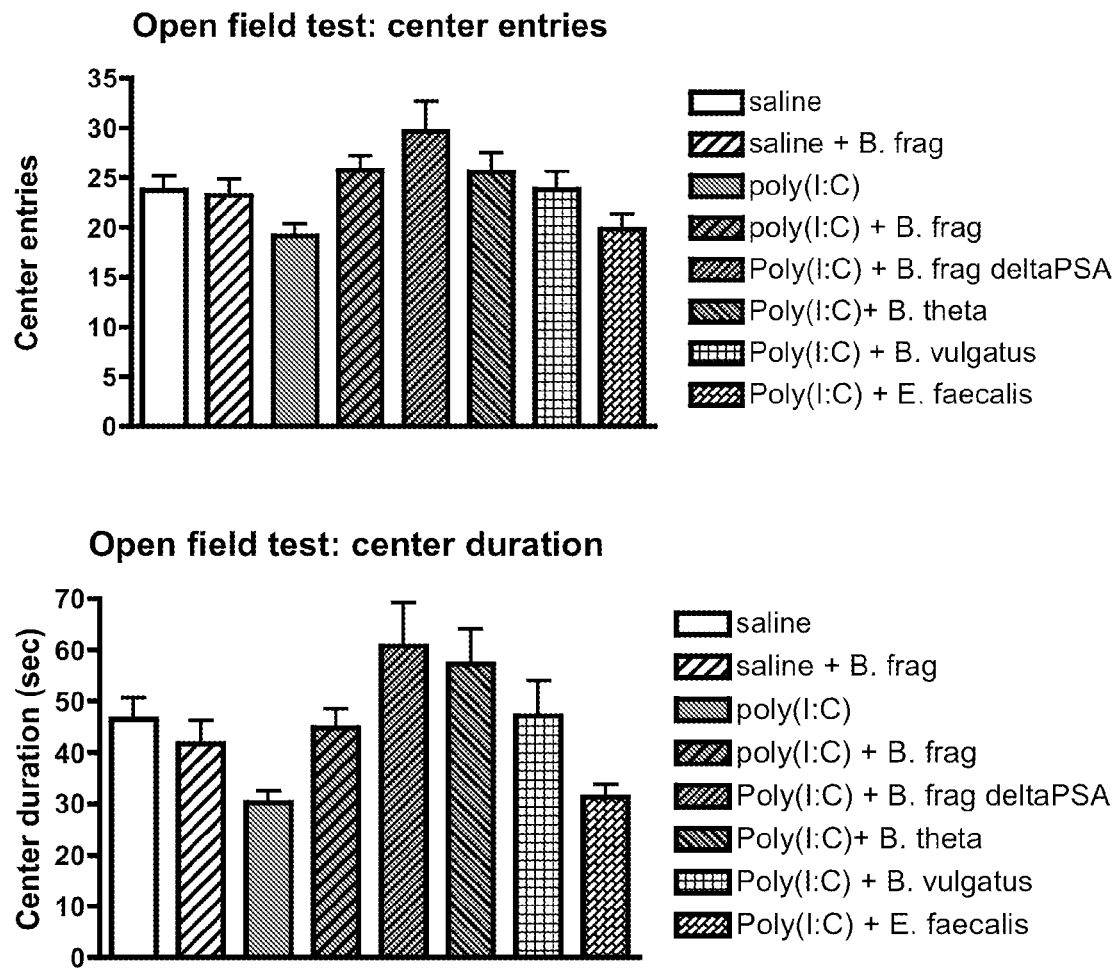
FIG. 1 shows that MIA offspring exhibit elevated anxiety in the open field test and that this can be alleviated by probiotic treatment. B. fragilis or other bacterial species were given in food for 1 week post-weaning (weaning is at 3 weeks of age).

The term "effective dose" is an amount that results in a reduction, inhibition or prevention of the behavioral disorder/abnormality/symptoms in the individual. The amount of B. fragilis or other probiotic required to achieve this can be determined by a person of skill in the art.

The term "individual" as used herein includes a single biological organism wherein inflammation can occur including but not limited to animals and in particular higher animals and in particular vertebrates such as mammals and in particular human beings.

The term "condition/disorder/symptom" or "behavioral abnormality" or as used herein means symptoms expressed by an individual with a mental disorder, such as but not limited to anxiety, autism, autism spectrum disorders, Fragile X, Rett syndrome, tuberous sclerosis, obsessive compulsive disorder, attention deficit disorder or schizophrenia. The aforementioned symptoms are some of those exhibited by the MIA offspring.

The term "individual in need of the treatment" means a person expressing or suffering from one or more of the behavioral disorder/symptoms mentioned above. An appropriately qualified person is able to identify such an individual in need of treatment using standard behavioral testing protocols/guidelines. The same behavioral testing protocols/guidelines can also be used to determine whether there is improvement to the individual's disorder/symptoms; and determine the most effective dose of the *B. fragilis* cell to give to an individual in need of the treatment.

The term "improvement in behavioral performance" as used herein means a prevention or reduction in the severity or frequency, to whatever extent, of one or more of the above behavioral disorder/symptoms/abnormalities expressed by the individual. The improvement is either observed by the individual taking the treatment themselves or by another person (medical or otherwise).

The term "treatment" as used herein indicates any activity that is part of a medical (prescribed by the physician) or non-medically approved (i.e. non-prescription including but not limited to vitamins, herbs; supplements; probiotics etc.) care that deals with a condition/symptom as described above.

The term "prevention" as used herein indicates any activity that reduces the burden of the individual later expressing those behavioral symptoms. This takes place at primary, secondary and tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by restoring function and reducing any condition/disorder/symptom or related complications.

Pharmaceutically acceptable or appropriate carriers can be, but not limited to, organic or inorganic, solid or liquid excipient which is suitable for the selected mode of application such as oral application or injection, and administered in the form of a conventional pharmaceutical preparation. Such preparation includes solid such as tablets, granules, powders, capsules, and liquid such as solution, emulsion, suspension and the like. Said carrier includes starch, lactose, glucose, sucrose, dextrin, cellulose, paraffin, fatty acid glyceride, water, alcohol, gum arabic and the like. If necessary, auxiliary, stabilizer, emulsifier, lubricant, binder, pH adjustor controller, isotonic agent and other conventional additives may be added.

The pharmaceutically acceptable or appropriate carrier may well include other compounds known to be beneficial to an impaired situation of the GI tract, (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

The term "nutraceutical" as used herein means a food stuff (as a fortified food or a dietary supplement) that provides health benefits. Nutraceutical foods are not subject to the same testing and regulations as pharmaceutical drugs.

The term "probiotic" as used herein means live microorganisms, which, when administered in adequate amounts, confer a health benefit on the host. The probiotics may be available in foods and dietary supplements (for example, but not limited to capsules, tablets, and powders). Examples of foods containing the probiotic are yogurt, fermented and unfermented milk, miso, tempeh, and some juices and soy beverages.

The term "extract" as used herein indicates either the insoluble material or soluble material obtained from the *B. fragilis* or related species using various chemical, immunological, biochemical or physical procedures known to those of skill in the art, including but not limited to, precipitation, centrifugation, filtering, column chromatography, and detergent lysis.

The term "whole cell lysate" refers to the fraction obtained when the *B. fragilis* or related species are lysed using detergent or other chemical or physical means.

The term "native" when used in connection with biological materials such as nucleic acid molecules, polypeptides, host cells, bacterial cells/strains and the like, refers to materials as they are found in nature and not manipulated by man.

The term "isolated" when used in connection biological materials such as nucleic acid molecules, polypeptides, bacterial cells, host cells, bacterial cells/strains and the like, refers to the isolated or purified aforementioned materials, where these materials do not occur naturally and/or where they have markedly different or distinctive characteristics compared to those found in the native material.

The term "non-denatured" is used herein refers to when the bacterial is frozen in a media and then undergoes a freeze-drying process. Such non-denatured bacteria can be mixed with other substances/compounds/carriers/additives and given in forms of a pill, tablet, or liquid to individuals in need of behavioral improvement. The non-denatured bacteria can also be mixed into foods (cookies, yogurt; milk etc.).

The term "conventional pharmaceuticals or compounds" as used herein in the context of "other conventional pharmaceuticals or compounds used to treat behavioral disorder/symptoms refers to those pharmaceuticals or compounds that persons of skill in the art (including but not limited to physicians) conventionally use to treat the above mentioned condition/disorder/symptom" or "behavioral abnormality.

The term "related" as used herein in the context of "*B. fragilis* and related species" refers to the other species under the genus *Bacteroides* (or otherwise), that were shown to have a positive effects on behaviors such as those tested here.

The Patterson laboratory developed a mouse model that has both construct and face validity for autism, MIA (maternal immune activation) (reviewed in Patterson, 2011). This is based on epidemiological evidence that viral or bacterial infection during pregnancy increases the risk for ASD in the offspring (Atladottir et al., 2010). In this animal model, pregnant mice that receive a respiratory infection at mid-gestation, or that receive the double-stranded RNA viral mimic, poly(I:C), produce offspring with a series of abnormal behaviors, including the hallmark symptoms of repetitive/compulsive behaviors, and deficits in social interaction and communication (Patterson, 2011). Moreover, MIA offspring display a specific neuropathology that is common in ASD, spatially restricted deficits in Purkinje cells (Patterson, 2011). Recently, the collaboration between the laboratories of Sarkis Mazmanian and Paul Patterson has discovered that the MIA offspring exhibit abnormalities in the immune system and the gastrointestinal tract. Most importantly, some of the ASD-like behavioral symptoms can be corrected or prevented by manipulating the microbiota of the MIA offspring. This treatment is based on prior work by the Mazmanian group showing the efficacy of *B. fragilis* treatment in several GI and systemic inflammatory disorders (Round et al., 2009, 2010).

Experiment 1. Colonization with *B. fragilis* Lowers Anxiety in Both MIA and Control Offspring The open field test is a test of anxiety under mildly stressful conditions, and ASD subjects exhibit enhanced anxiety under such circumstances. The offspring are tested in the open field to determine the effects of *B. fragilis* and a number of other bacterial species on anxiety behavior. Groups of pregnant mice (n>3) are treated on E12.5 with poly(I:C) to induce MIA, or saline as the control (Smith et al., 2007). Immediately upon weaning the offspring are colonized with one of the bacteria shown (given in food) or not, for one week. Mice are placed in a brightly lit open box, and activity is recorded by a video camera and analyzed using Ethovision software (Noldus). The number of entries into, and the time spent in, the center of the arena are measured. As expected, MIA offspring spend less time in the center of the open field and enter it less often than control offspring, indicating increased anxiety (FIG. 1). Treatment with *B. fragilis* and other *Bacteroides* species prevents the abnormal behavior in the MIA offspring, indicating that this probiotic treatment lowers anxiety in normal animals as well as in the ASD model mice. In contrast, the non-*Bacteroides* species, *E. faecalis*, is not able to prevent anxiety in the MIA offspring. Thus, there is specificity among the bacterial species tested (the differences cited are significant at $p<0.05$ and 0.01).

2. The GI Tract of MIA Offspring Displays Pathology

Figure 2:
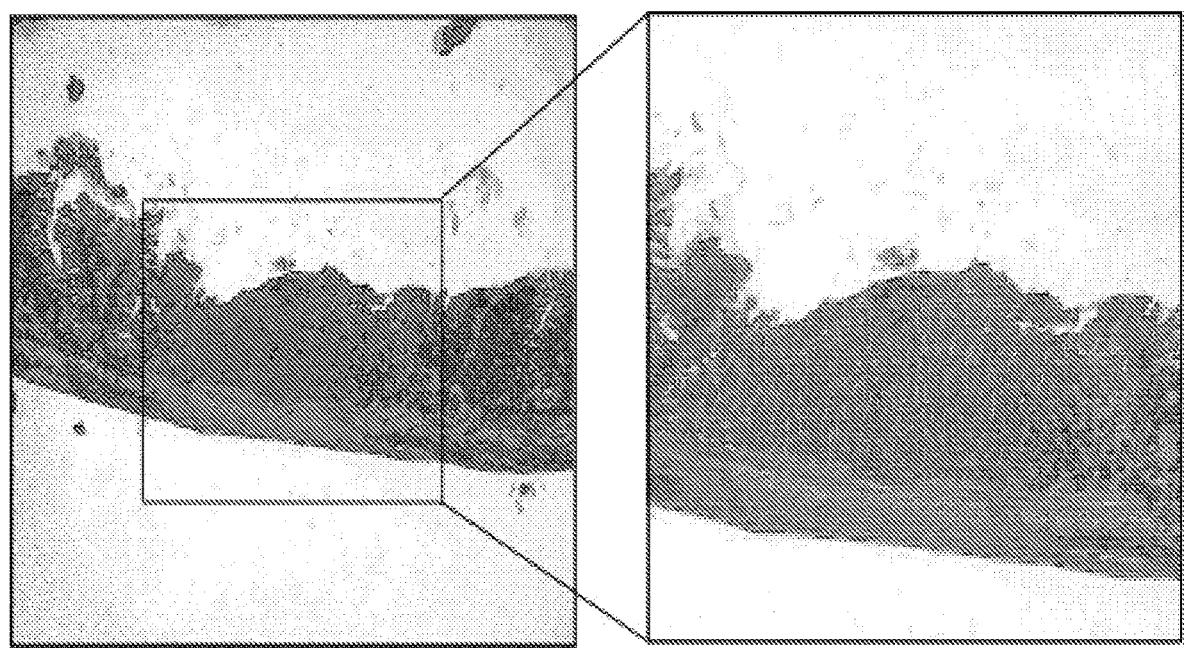
FIG. 2 shows histological evidence that adult MIA offspring exhibit greater inflammatory cell infiltration of their colons. The inset shows a magnified view of an inflammatory cell aggregate.

The colons of adult MIA and control offspring were prepared for histology and stained with H & E. As illustrated in FIG. 2, there is a very significant cellular infiltration in MIA offspring. This was seen in 4 out of 5 MIA mice examined. In contrast, this type of infiltration was seen in only 1 out of 5 control mice. The identity of the cells infiltrating the colon is being examined.

Figure 3:
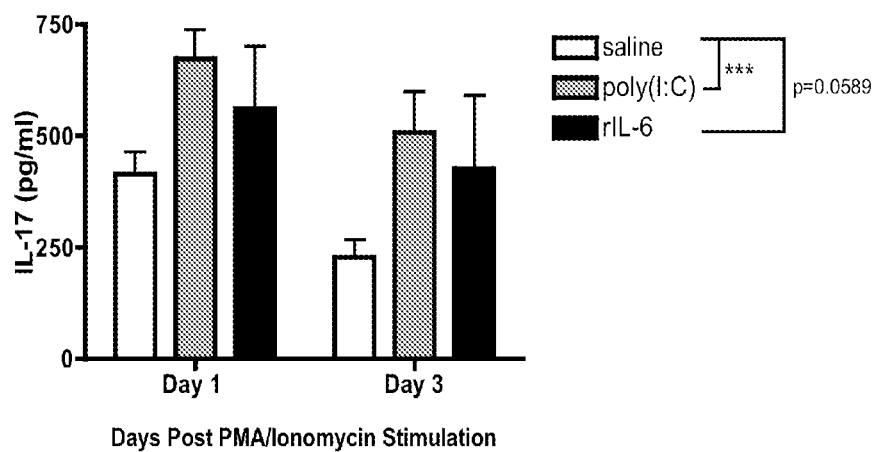
FIG. 3 shows elevated IL-17 levels in lymphocytes of MIA offspring. In this case, MIA was induced in the pregnant mice by treatment with either poly(I:C) or a single injection of recombinant IL-6. The cytokine IL-6 was previously shown to induce the same ASD-like symptoms in the resulting offspring as maternal poly(I:C) injection (Smith et al., 2007).

3. Lymphocytes in GI-Associated, Mesenteric Lymph Nodes from Offspring of MIA Mothers Display Elevated Cytokine Release upon Stimulation To assess the activation state of lymphocytes associated with the GI tract, mesenteric lymph nodes were dissected from adult offspring of control mothers, offspring of MIA mothers treated with poly(I:C), and offspring of MIA mothers treated with IL-6. CD4+ cells were isolated and treated in culture with PMA and ionomycin. Supernatants were assayed for IL-6 (not shown) and IL-17 (FIG. 3). On both days assayed, the lymphocytes from MIA offspring display higher cytokine release than controls.

4. Marble Burying Test

Figure 4:
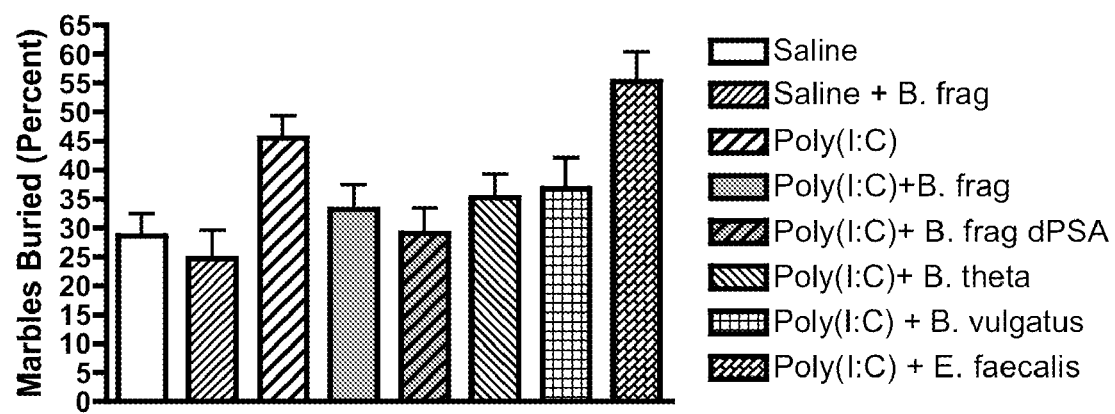
FIG. 4 shows that MIA offspring exhibit elevated levels of stereotyped/repetitive behavior in the marble burying tests, and that this can be normalized by probiotic treatment with certain bacteria. Adult offspring of saline- and poly(I:C)-injected mothers were tested for the percent of marbles buried in a 10 min period. B. fragilis and related species colonization at weaning prevents development of repetitive and compulsive behaviors compared to MIA offspring without the probiotic. Student's t-test: *$p<0.05$. **$p<0.01$. n=14-20 animals per trial.

One of the tests used to assay stereotyped, repetitive/compulsive behavior in rodents is marble burying. Animals are placed in a cage with a series of marbles located on top of the bedding. The number of marbles buried in a given period is measured to quantify this repetitive behavior. We find that MIA offspring bury many more marbles than controls (FIG. 4 saline vs. poly(I:C)). Remarkably, MIA offspring treated with *B. fragilis* or other *Bacteroides* species do not display this ASD-like symptom (FIG. 4). Moreover, as in the open field test, treatment with the non-*Bacteroides* species, *E. faecalis*, does not prevent anxiety in the MIA offspring. (The differences cited are significant at $p<0.05$)

5. Restoration of Epithelial Barrier Function

Figure 5:
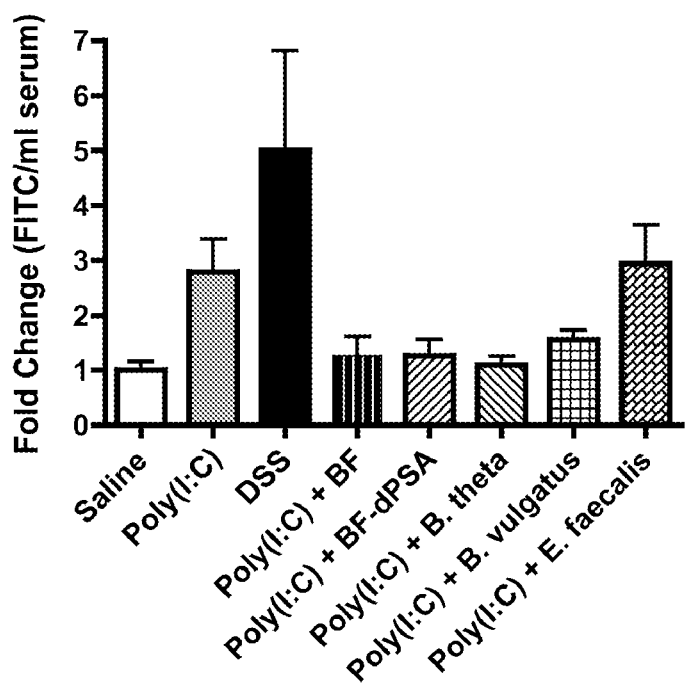
FIG. 5 shows the extent of dextran probe leakage into the circulation of MIA offspring given one of several types of bacterial species. Most important is the finding that MIA display a "leaky gut" syndrome and that B. fragilis and the other Bacteroides species tested can prevent this disorder.

Since *Bacteroides* species can prevent behavioral ASD-like abnormalities in the MIA offspring, and these offspring display GI pathology, it was of interest to ask if the probiotics also prevent the GI symptoms. GI epithelial barrier function can be tested by gavaging the mouse with a labeled dextran that is large enough such that it does not normally leak through the barrier in significant amounts. When barrier function is compromised as by gavaging with dextran sodium sulfate (DSS), the labeled dextran probe does leak into the circulation (FIG. 5). This is the positive control for "leaky gut", a symptom found in a large subset of ASD children.

Importantly, the adult MIA offspring also display very significant levels of leaky gut, and this can be prevented by post-weaning treatment with all of the *Bacteroides* species tested, but not with the non-*Bacteroides*, *E. faecalis* (FIG. 5). Thus, the efficacy of probiotic therapy in the GI tract corresponds with the specificity of the behavioral therapy.

Given the above results, the similarities between the MIA model and the respective human disorders (including the cardinal behavioral symptoms of ASD and neuropathology characteristic of ASD, and behavior and neuropathology characteristic of schizophrenia, which both share the maternal infection risk factor; reviewed in Patterson, 2011), we would expect that individuals in need of treatment could be given *B. fragilis* or related bacteria in a capsule, pill, nutraceutical, or other probiotic form, and the individual would show signs of improved behavioral performance. The effective dose for such an individual could be determined easily by the individual undergoing the treatment themselves or by another individual. For instance, the individuals themselves could determine whether their symptoms of anxiety were improved upon taking the appropriate amount of the probiotic. The individuals in need of such treatment could take the probiotic when needed or prior to the time they expect an occurrence of the behavioral abnormality would occur, for instance, when the individual believes the upcoming day would be stressful.

The following references are hereby incorporated by reference in their entirety:

Atladottir, H. O., Thorsen, P., Ostergaard, L., Schendel, D. E., Lemcke, S., Abdallah, M., Pamer, E. T. 2010. Maternal infection requiring hospitalization during pregnancy and autism spectrum disorders. *J Autism Devel Dis* 40:1423-1430.

Buie, T., D. B. Campbell, G. J. Fuchs, 3rd, G. T. Furuta, J. Levy, J. Vandewater, A. H. Whitaker, D. Atkins, M. L. Bauman, A. L. Beaudet, E. G. Carr, M. D. Gershon, S. L. Hyman, P. Jirapinyo, H. Jyonouchi, K. Kooros, R. Kushak, P. Levitt, S. E. Levy, J. D. Lewis, K. F. Murray, M. R. Natowicz, A. Sabra, B. K. Wershil, S. C. Weston, L. Zeltzer, and H. Winter. 2010. Evaluation, diagnosis, and treatment of gastrointestinal disorders in individuals with ASDs: a consensus report. *Pediatrics* 125 *Suppl* 1:51.

Patterson, P. H. 2011. Modeling features of autism in animals. *Pediatric Res* 69:34R-40R.

Round, J. L., and S. K. Mazmanian. 2009. The gut microbiota shapes intestinal immune responses during health and disease. *Nat Rev Immunol* 9:313.

Round, J. L., R. M. O'Connell, and S. K. Mazmanian. 2010. Coordination of tolerogenic immune responses by the commensal microbiota. *J Autoimmun* 34:1220.

Smith, S. E., J. Li, K. Garbett, K. Mimics, and P. H. Patterson. 2007. Maternal immune activation alters fetal brain development through interleukin-6. *J Neurosci* 27:10695.

The invention claimed is:

1. A method for ameliorating Rett syndrome or a symptom thereof in a subject in need thereof, consisting of administering to the subject a single composition comprising a single *Bacteroides* bacteria species, wherein the bacterial species is *B fragilis*, *B. thetaiotaomicron*, or *B. vulgatus*.

2. The method of claim 1, wherein the composition is a tablet, a granule, a powder, a capsule, a liquid, or a food composition.

3. The method of claim 1, wherein the bacteria is *B. fragilis*.

4. The method of claim 1, wherein the subject displays leaky gut.

5. The method of claim 1, wherein the subject shows improved leaky gut after the subject is administered the composition.

6. The method of claim 1, wherein the composition further comprises a pharmaceutically acceptable carrier.

7. The method of claim 6, wherein the pharmaceutically acceptable carrier is a stabilizer, antioxidant, emulsifier, lubricant, binder, pH adjustor controller, or isotonic agent.

8. The method of claim 6, wherein the pharmaceutically acceptable carrier comprises one or more of starch, lactose, glucose, sucrose, dextrin, cellulose, paraffin, glyceride, water, alcohol, or gum arabic.

9. The method of claim 1, further comprising one or more of vitamin C, vitamin E, selenium, or zinc.

10. The method of claim 1, wherein the single *Bacteroides* bacteria species is provided in milk, yogurt, curd, cheese, unfermented milk, fermented milk, milk-based fermented product, ice cream, fermented cereal based product, milk-based powder, infant formula, miso, tempeh, a soy beverage, liquid suspension, dried oral supplement, or a wet oral supplement.

11. The method of claim 1, wherein the composition comprises a juice or soy beverage.

* * * * *